(12) United States Patent
Tsuchiya et al.

(10) Patent No.: US 7,727,524 B2
(45) Date of Patent: Jun. 1, 2010

(54) LOW SODIUM LIQUID SEASONING WITH ANTI-HYPERTENSIVE ACTIVITY

(75) Inventors: Shigemi Tsuchiya, Sumida-ku (JP); Youko Seo, Sumida-ku (JP); Jun Kohori, Sumida-ku (JP); Ryuji Ochiai, Haga-gun (JP); Atsushi Suzuki, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/270,511

(22) Filed: Nov. 10, 2005

(65) Prior Publication Data

US 2006/0115517 A1    Jun. 1, 2006

(30) Foreign Application Priority Data

Nov. 12, 2004 (JP) .............................. 2004-329849
Dec. 14, 2004 (JP) .............................. 2004-361318
Aug. 29, 2005 (JP) .............................. 2005-248206

(51) Int. Cl.
*A61K 9/00* (2006.01)
*A61K 35/00* (2006.01)
*A61K 31/198* (2006.01)
*A61K 47/00* (2006.01)
*A23D 9/013* (2006.01)
*A23L 1/221* (2006.01)
*A23J 1/00* (2006.01)
*A01N 61/00* (2006.01)

(52) U.S. Cl. ...................... 424/115; 424/400; 424/439; 426/531; 426/650; 426/656; 514/1; 514/566

(58) Field of Classification Search ........................ None
See application file for complete search history.

(56) References Cited

U.S. PATENT DOCUMENTS

| 4,593,045 | A | * | 6/1986 | Flork et al. | ................. 514/562 |
| 5,562,942 | A |   | 10/1996 | Koh et al. | |
| 5,908,653 | A | * | 6/1999 | Stute et al. | ................. 426/589 |

(Continued)

FOREIGN PATENT DOCUMENTS

JP          59-055165 A       3/1984

(Continued)

OTHER PUBLICATIONS

Nakamura et al., "Feasibility and Effect on Blood Pressure of 6-Week Trial of Low Sodium Soy Sauce and Miso (Fermented Soybean Paste)" Jun. 2003, Circ J, 67:530-534.*

(Continued)

*Primary Examiner*—Christopher R Tate
*Assistant Examiner*—Aaron J Kosar
(74) *Attorney, Agent, or Firm*—Oblon, Spivak, McClelland, Maier & Neustadt, L.L.P.

(57) ABSTRACT

The present invention provides a liquid seasoning, which brings on a sufficient salty taste although it has a low sodium concentration, and which exhibits for example a pharmacological effect such as an antihypertensive effect at a high level. The present invention relates to a liquid seasoning, which contains the following components (A) to (D):
 (A) 3.55% or less by weight of sodium;
 (B) 0.5% to 4.2% by weight of potassium;
 (C) more than 2% by weight of an acidic amino acid and/or more than 1% by weight of a basic amino acid; and
 (D) 0.05% to 10% by weight of a food material having an antihypertensive effect.

26 Claims, 3 Drawing Sheets

U.S. PATENT DOCUMENTS

| | | | |
|---|---|---|---|
| 6,159,529 | A | 12/2000 | Uchida et al. |
| 6,379,717 | B1* | 4/2002 | Hattori ........................ 424/750 |
| 6,423,309 | B1* | 7/2002 | Tsusaki et al. ............. 424/93.4 |
| 2002/0054923 | A1* | 5/2002 | Suzuki et al. ............... 424/729 |
| 2002/0106424 | A1 | 8/2002 | Ogawa et al. |
| 2005/0123670 | A1* | 6/2005 | Vasquez ..................... 426/649 |
| 2008/0003314 | A1* | 1/2008 | Ochiai et al. ................ 424/776 |
| 2008/0008812 | A1* | 1/2008 | Ochiai et al. ................ 426/542 |

FOREIGN PATENT DOCUMENTS

| | | | |
|---|---|---|---|
| JP | 64-013968 | A | 1/1989 |
| JP | 04-108358 | A | 4/1992 |
| JP | 5-7987 | | 1/1993 |
| JP | 6-97972 | | 12/1994 |
| JP | 7-227245 | | 8/1995 |
| JP | 2675254 | | 7/1997 |
| JP | 10-66540 | | 3/1998 |
| JP | 11-187841 | | 7/1999 |
| JP | 2001-245627 | | 9/2001 |
| JP | 2001-352940 | | 12/2001 |
| JP | 2002-165577 | | 6/2002 |
| JP | 2002-233326 | A | 8/2002 |
| JP | 2002-300862 | | 10/2002 |
| JP | 2002-345430 | A | 12/2002 |
| JP | 2002-360289 | | 12/2002 |
| JP | 2003-169659 | | 6/2003 |
| JP | 2004-147560 | | 5/2004 |
| JP | 2004-187501 | | 7/2004 |
| JP | 2004-194515 | * | 7/2004 |
| JP | 2004-194515 | A * | 7/2004 |
| JP | 2004-290088 | A | 10/2004 |
| JP | 2004-290129 | | 10/2004 |

OTHER PUBLICATIONS

Yamasa, "Naturally Brewed Yamasa Less Salt Soy Sauce" Yamasa Corporation USA <http://www.yamasausa.com/Yamasa_products_retail.htm> online archive Oct. 3, 2003, accessed Aug. 16, 2007.).*

Nakamura, Mieko, et al. "Feasability and Effect on Blood Pressure of 6-Week trial of Low-Sodium Soy Sauce and Miso (Fermented Soybean Paste)", Circulation Journal.2003, 67, 530-534.*

Yamasa "Naturally Brewed Yamasa Less Salt Soy Sauce" Yamasa Corporation USA <http://www.yamasausa.com/Yamasa_products_retail.htm> Oct. 3, 2003 (accessed online archive Aug. 16, 2007), 5 pages.*

Yamaguchi, Shizuko and Ninomiya, Kumiko. "The Use and Utility of Glutamates as Flavoring Agents in Food: Umami and Food Palatability", Journal of Nutrition. 2000, 130, pp. 921S-926S.*

Ajinomoto, "Food and Amino Acids" Encyclopedia of Amino Acids. <http://web.archive. org/web/20030812102616/http://www.ajinomoto.com/amino/eng/food.html> archived online Aug. 12, 2003 (accessed Feb. 28, 2008), 3 pages.*

Cotner, Sam. "Organic Compounds" Plant Tissue Culture Network <http://web.archive.org/web/20010522165515/http://aggie-horticulture.tamu.edu/tisscult/database/media/organic.html> archived online May 22, 2001 (accessed Feb. 28, 2008), 3 pages.*

Schwarz, K. et al. "Investigation of Plant Extracts for The Protection of Processed Foods Against Lipid Oxidation. Comparison of Antioxidant Assays Based on Radical Scavenging, Lipid Oxidation and Analysis of the Principal Antioxidant Compounds", Eur Food Res Technol (2001) 212 :319-328.*

U.S. Appl. No. 11/436,517, filed May 19, 2006, Tsuchiya, et al.

U.S. Appl. No. 11/271,790, filed Nov. 14, 2005, Tsuchiya, et al.

U.S. Appl. No. 11/180,734, filed Jul. 14, 2005, Tsuchiya, et al.

Yanyan Wu, et al., "Experimental preparation of nutrient liquid from shellfish *Pinctada martersii* meat and nutritional evaluation" Journal of Shanghai Fisheries University, vol. 12, No. 4, Dec., 2000, pp. 313-318.

Chaohua Zhang, et al., "Nutrients and composition of free amino acid in edible part of *Pinctada martensii*", Journal of Fisheries of China, vol. 24, No. 2, Apr., 2000, pp. 180-184.

Kai-cheng Zhang, "Study progress in bitterness mechanism and bitterness depressant technique", China Condiment, No. 11, pp. 39-42.

* cited by examiner

LOW SODIUM LIQUID SEASONING WITH ANTI-HYPERTENSIVE ACTIVITY

BACKGROUND OF THE INVENTION

1. Field of the Invention

The present invention relates to a liquid seasoning.

2. Background of the Invention

Nowadays, interest in physiological functions of various components contained in food products is increasing. The Ministry of Health, Labor, and Welfare in Japan routinely grants permission for food products containing components associated with such physiological functions or biological activities as Food for Specified Health Use (FOSHU). Such food products have been commercialized in the form of a beverage, yogurt, soup, miso soup, a prepared food product such as hamburger steak, a tablet-form confectionery, a tablet or the like. It has been recommended that these food products be ingested once or twice a day.

Various materials have been proposed as materials having physiologically active functions. An example is a food material having an antihypertensive effect. Among others, peptide, γ-aminobutyric acid, chlorogenic acid, or the like are present as substances that are contained in food products and are highly safe. Thus, techniques of increasing the contents of such substances in food products or adding such substances to food products have been proposed (JP-A-2004-147560, JP-A-2003-169659, JP-A-2001-352940, JP-A-07-227245).

Based on the view that common salts have adverse effects on renal diseases, cardiac diseases, and hypertension, it has been proposed to add a food material having an antihypertensive effect to food products containing a high content of common salts. There have been a large number of techniques regarding the combined use of such a food material having an antihypertensive effect with soy sauce as a representative example of the aforementioned food products (JP-A-2004-290129, JP-A-2004-187501, JP-A-2002-360289, JP-A-2002-300862, JP-A-2004-194515). In order to ingest an effective amount of such food material, it is necessary to ingest a large amount of the food product. However, such ingestion amounts to ingestion of large quantities of salts. This leads to an unfavorable consequence because the ingesting effect of said food material is decreased. Furthermore, the addition of a large amount of the aforementioned food material may affect the flavor of the food product.

SUMMARY OF THE INVENTION

The present invention provides a liquid seasoning, which contains the following components (A) to (D):

(A) 3.55% or less by weight of sodium;
(B) 0.5% to 4.2% by weight of potassium;
(C) more than 2% by weight of acidic amino acid and/or more than 1% by weight of basic amino acid; and
(D) 0.05% to 10% by weight of a food material having an antihypertensive effect.

DETAILED DESCRIPTION OF THE INVENTION

Figure 1:
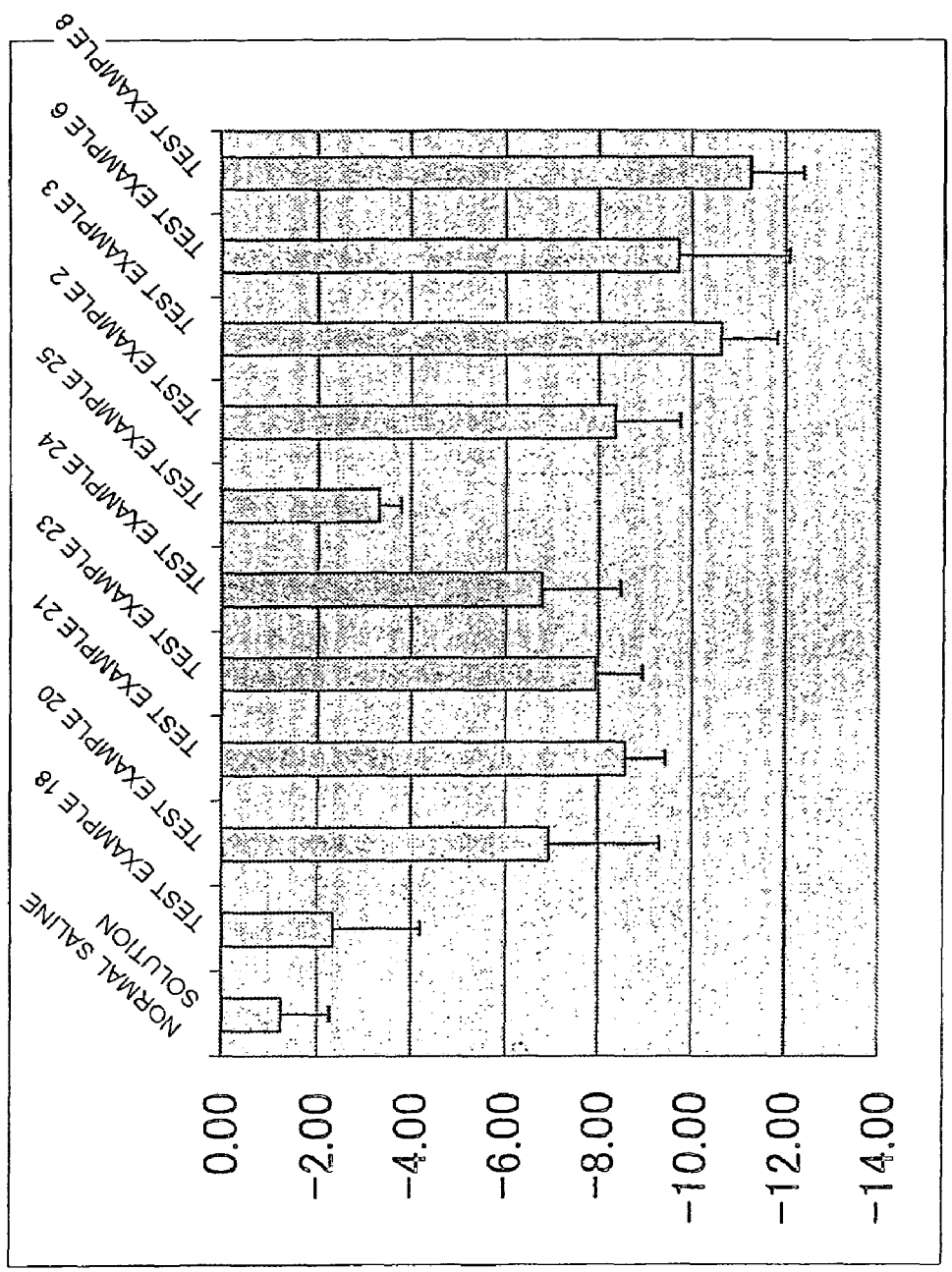
FIG. 1 shows the rate of change (%) of the systolic blood pressure of a rat, which was measured 6 hours after ingestion of the example liquid seasoning of the present invention.

In any conventional technique mentioned above, there remains a problem regarding flavor when a food material having an antihypertensive effect is used with the combination of a food product containing high quantities of common salts, and a problem regarding ingestion of high quantities of common salts that occurs when such a food product is ingested in high volume. Hence, it is still considered unfavorable to continuously ingest the aforementioned food product. In particular, when the aforementioned food material is used in combination with low salt food products including low salt soy sauce as a typical example, the obtained food product is poorly satisfactory in terms of its salty taste, and thus another problems arises for the enhancement of the salty taste. There have been various techniques intended for improving the flavor of such a low common salt food product (JP-B-2675254, JP-B-06-97972, JP-A-10-66540, JP-A-2001-245627, JP-A-2002-165577, JP-B-05-007987, JP-A-11-187841). Although these techniques proved to have certain effects, it cannot be said that such effects are sufficient. In particular, it cannot be said that such effects are sufficient in terms of a good balance between a decrease in a common salt concentration and the maintenance of a salty taste.

The present invention provides a liquid seasoning produced by combining a liquid seasoning including soy sauce as a typical example of food which is ingested on a daily basis with a food material having an antihypertensive effect, which improves the flavor, facilitates continuous ingestion, and exhibits for example a pharmacological effect such as an antihypertensive effect at a high level.

With regard to a liquid seasoning containing a food material having an antihypertensive effect, the present inventors have conducted studies regarding a means for improving the flavor and also bringing on a salty taste although the sodium concentration thereof is set at 3.55% or less by weight (the common salt concentration thereof is set at 9% or less by weight). As a result, the inventor has found that when specific amounts of certain amino acid(s) are added to a system containing 3.55% or less by weight of sodium (9% or less by weight of common salt) and 0.5% to 4.2% by weight of potassium, a liquid seasoning, the flavor is not deteriorated although a food material having an antihypertensive effect is added thereto. The liquid seasoning also provides a stronger salty taste and a good taste. The inventors have also found that this liquid seasoning can be continuously ingested and has an effective antihypertensive effect.

The present invention provides a liquid seasoning containing 3.55% or less by weight of sodium (9% or less by weight of common salt), whose flavor is not deteriorated although a food material having an antihypertensive effect is added thereto; and which brings on a sufficiently strong salty taste, facilitates continuous ingestion, and exhibits a pharmacological effect such as an antihypertensive effect at a high level. The liquid seasoning of the present invention is useful as a low salt soy souse.

The term "low salt soy sauces" is used in the present application to mean "soy sauce" and "soy sauce processed food," wherein the sodium content in 100 g of such a product is 3,550 mg or less (9 g of common salts). Thus, this term is not limited to special use foods for patients defined by the Nutrition Improvement Law of JAPAN. The term "soy sauce"

is a liquid seasoning defined by the Japanese Agricultural Standard (JAS), and the term "soy sauce processed food" is also a liquid seasoning, which is produced by adding a seasoning, an acidulant, a flavor, a broth, extracts, etc., to the soy sauce that complies with the Japanese Agricultural Standard (JAS), and which is used for the same purpose as that of "soy sauce." Herein, the term "soy sauce" used in the present application has the same concept as that of the "soy sauce" defined by the Japanese Agricultural Standard (JAS). In addition, the term "liquid seasoning" used in the present application has a concept which includes seasonings that comply with the requirements of the present application, although they deviate from standards as the aforementioned low salt soy sauces and low salt soy sauce. In the field of liquid seasoning manufacturing, the content of a mixed substance is generally indicated by w/v %. In the present application, however, the amount of each component mixed is indicated by % by weight based on the total weight of a liquid seasoning. In this case, in the case of the nitrogen content in soy sauce for example, "1.6% by weight" corresponds to "1.9 w/v %."

The content of sodium (A) in the liquid seasoning of the present invention is set at 3.55% or less by weight. However, it is preferably between 2.75% and 3.5% by weight, and more preferably between 3.1% and 3.4% by weight, in terms of the antihypertensive effect and flavor (sufficient salty taste). It is to be noted that the term "content" is used in the present invention to mean the ratio of a component in the total amount of the liquid seasoning, unless otherwise specified. The common salt may be used as sodium (A) in the liquid seasoning of the present invention. The content of common salt in the liquid seasoning of the present invention is set at 9% or less by weight. It is preferably between 7% and 9% by weight, and more preferably between 8% and 9% by weight, in terms of an antihypertensive effect and flavor (sufficient salty taste).

The content of potassium (B) in the liquid seasoning of the present invention is set between 0.5% and 4.2% by weight. However, in order to increase the salty taste in spite of a low sodium content and to prevent a bitter taste, it is preferably between 1% and 3.6% by weight, and more preferably between 1.5% and 3.1% by weight. In addition, potassium chloride is preferably used because it has a salty taste and a very little abnormal taste. When potassium chloride is used, it is preferably mixed in a liquid seasoning at a weight ratio between 1% and 7% by weight, more preferably between 2% and 6% by weight, and even more preferably between 3% and 5% by weight, based on the total weight thereof.

In order to adjust the content of sodium and that of potassium to the aforementioned ranges, the following methods may be applied, for example: a method of producing soy sauce using a mixed solution consisting of common salt and potassium chloride, for example, as mother water; a method of mixing soy sauce obtained using only a potassium chloride solution as mother water, with soy sauce obtained using only a saline solution as mother water; and a method of subjecting common soy sauce obtained using a saline solution as mother water to electrodialysis or membrane treatment, so as to eliminate sodium, and then adding potassium chloride to the desalted soy sauce.

With regard to the contents of amino acid(s) (C) in the liquid seasoning of the present invention, the content of acidic amino acid is set at more than 2% by weight, and/or basic amino acid is set at more than 1% by weight. However, the content of acidic amino acid is preferably from more than 2% to 5% by weight, more preferably between 2.4% and 4.5% by weight, and even more preferably between 2.5% and 3.8% by weight, in terms of the duration of salty taste. The content of basic amino acid is preferably from more than 1% to 3% by weight, more preferably between 1.2% and 2.5% by weight, and even more preferably between 1.5% and 2% by weight, in terms of the duration of salty taste. In addition, the liquid seasoning of the present invention is preferably based on a fermented seasoning, in terms of the duration of salty taste, flavor, and the like. In such a case, amino acid(s) (C) include those derived from the raw material soy sauce, and in a case where the contents of such amino acids are less than the aforementioned ranges, acidic amino acid salts, basic amino acid salts, or the like are preferably added, separately. The term "acidic amino acid and/or basic amino acid" is used in the present invention to mean free amino acids or amino acids that are in the form of amino acid salts. The content of amino acid indicates a value of free amino acid and a value of converting amino acid salts into free amino acid in the present invention.

Moreover, in the liquid seasoning of the present invention, among acidic amino acids and/or basic amino acids, aspartic acid and glutamic acid as acidic acids are preferable in terms of the duration of salty taste. The combined use of aspartic acid with glutamic acid is more preferable in terms of the duration of salty taste. In this case, the content of aspartic acid is preferably between 1% and 3% by weight, more preferably between 1.2% and 2.5% by weight, and even more preferably between 1.2% and 2% by weight, in terms of the duration of salty taste. When the liquid seasoning is based on a fermented seasoning, such aspartic acid also includes those derived from the raw material. When the content of aspartic acid is less than the aforementioned range, L-aspartic acid, sodium L-aspartate, or the like are preferably added, separately. On the other hand, the content of glutamic acid is preferably between 1% and 2% by weight, more preferably between 1.2% and 2% by weight, and even more preferably between 1.3% and 1.8% by weight, in terms of the duration of salty taste. When the liquid seasoning is based on a fermented seasoning, such glutamic acid also includes those derived from the raw material. When the content of glutamic acid is less than the aforementioned range, L-glutamic acid, sodium L-glutamate, or the like are preferably added, separately.

Examples of basic amino acids include lysine, arginine, histidine, and ornithine. Of these, lysine and histidine are preferable, and histidine is more preferable. The content of lysine is preferably between 0.5% and 1% by weight in terms of the feeling of stimulation of salty taste. The content of histidine is preferably between 0.2% and 2% by weight, and more preferably between 0.5% and 1% by weight, in terms of an increase in salty taste and the duration thereof. When the liquid seasoning is based on a fermented seasoning, these basic amino acids also include those derived from the raw material. When the content of the basic amino acid is less than the aforementioned range, it is preferably added separately.

In the liquid seasoning of the present invention, the weight ratio of aspartic acid/potassium (B) is preferably 0.25 or greater, more preferably 0.3 or greater, even more preferably 0.46 or greater, and even more preferably 0.5 or greater, in terms of the elimination of the bitter taste caused by potassium chloride.

In the liquid seasoning of the present invention, in order to increase the salty taste in spite of a low sodium or common salt content and to prevent a bitter taste, the content of nitrogen is preferably 1.2% or more by weight. In addition, the content of nitrogen is more preferably 1.3% or more by weight, even more preferably 1.4% or more by weight, even more preferably between 1.4% and 2% by weight, and even more preferably between 1.6% and 2% by weight. In general, a high content of nitrogen in soy sauce results in a mild taste, thereby decreasing the salty taste. However, it has been totally unexpected that when acidic amino acid and/or basic amino acid, and in particular, aspartic acid and glutamic acid, are added at specific amounts to soy sauce containing a small amount of sodium or common salt and potassium, and when the total content of nitrogen therein is adjusted to the aforementioned range, the salty taste can be improved.

The nitrogen content in common soy sauce is between 1.2% and 1.6%. A nitrogen content of 1.6% or higher may be achieved by a step of adding amino acids, preferably acidic amino acid and/or basic amino acid, and more preferably aspartic acid and/or glutamic acid, to soy sauce brewed by common methods, to the range defined in the present invention, or by subjecting the above soy sauce to a concentration or desalination step. For example, there may be applied: a method, which includes eliminating sodium or common salt by vacuum concentration, and at the same time, adjusting the dilution rate of volatile components containing water as a main component; or a method of simultaneously concentrating nitrogen, utilizing the transition of ion-bounded water that occurs during elimination of sodium or common salt with an electrodialysis device. Moreover, there may also be applied: a method of increasing the nitrogen content by concentrating with RO membrane or vacuum concentration, low salt soy sauce with a lower common salt concentration than those of ordinary products; a method of desalting soy sauce with a high nitrogen content, such as tamari soy sauce or re-mashed soy sauce; and other methods ("Zoho Shoyu no Kagaku to Gijutsu (Enlarged Edition, Science and Technology of Soy Sauce)," T. Tochikura, Brewing Society of Japan, 1994).

In the liquid seasoning of the present invention, the weight ratio of aspartic acid content/nitrogen content in the above liquid seasoning, from which component (D) is excluded, is preferably 0.5 or greater, more preferably 0.6 or greater, and even more preferably 0.7 or greater, in terms of an increase in salty taste and the improvement of sharpness of the taste.

A food material (D) having an antihypertensive effect is preferably one or more selected from among polyphenols, a peptide having angiotensin converting enzyme inhibitory activity, and a sympathoinhibitory substance.

Specifically, such polyphenols may preferably be phenol substances, to the benzene ring of which one or more, and preferably two or more hydroxyl groups are bound. Examples of such substances include flavonoid, tannin, and phenolic acid, which are derived from plants. In addition, glycosides of these substances may also be used. More preferred examples of polyphenols include caffeoylquinic acids, feruloylquinic acid, flavonols, flavanols, flavanones, flavones, isoflavones, and anthocyanidins. Specific examples include catechin, epicatechin, gallocatechin, epigallocatechin, rutin, quercitrin, isoquercitrin, quercetin, myricitrin, myricetin, daizein, daizin, glycitein, glycitin, genistein, genistin, myricitrin, hesperidin, methylhesperidin, neohesperidin, hesperetin, naringin, naringenin, prunin, astragalin, kaempferol, apiin, apigenin, delphinidin, delphin, nasunin, peonidin, peonin, petunin, peonidin, malvidin, malvin, enin, cyanidin, leucocyanidin, cyanin, chrysanthemin, keracyanin, idein, mecocyanin, pelargonidin, callistephin, a derivative thereof, and a mixture consisting of two or more selected from among the aforementioned substances. Examples of such a derivative include an acetylated product, a malonylated product, a methylated product, and a sugar-binding product. A sugar-binding product, in which one or more molecules of sugars, such as glucose, rhamnose, galactose, rutinose, neohesperidose, or apiosyl glucose, bind to one molecule of polyphenol via a covalent bond is preferred. Preferably 1 to 20, more preferably 2 to 10 molecules of such sugars bind to the above polyphenol. Of these, caffeoylquinic acids are preferable because they have a stable and permanent antihypertensive effect. In addition, the polyphenols in the present invention includes the compounds which substituted a part or all of the methoxyl groups for hydroxy groups in the polyphenol molecules.

Such caffeoylquinic acids include isomers and analogs. In the present invention, pure isomers, analogs, or mixtures thereof may be used. Specific examples of caffeoylquinic acids used in the present invention include 3-caffeoylquinic acid, 4-caffeoylquinic acid, 5-caffeoylquinic acid (chlorogenic acid), 3,4-dicaffeoylquinic acid, 3,5-dicaffeoylquinic acid, 4,5-dicaffeoylquinic acid, 3-feruloylquinic acid, 4-feruloylquinic acid, 5-feruloylquinic acid, and 3-feruloyl-4-caffeoylquinic acid.

When caffeoylquinic acids are converted to salts, they are able to improve water solubility and thereby increase physiological effectiveness. Such salts are preferably pharmacologically acceptable salts. Examples of a basic substance used for forming such salts include: alkaline metal hydroxides such as lithium hydroxide, sodium hydroxide, or potassium hydroxide; alkaline-earth metal hydroxides such as magnesium hydroxide or calcium hydroxide; inorganic bases such as ammonium hydroxide; basic amino acids such as arginine, lysine, histidine, or ornithine; and organic bases such as monoethanolamine, diethanolamine, or triethanolamine. Among these, alkaline metal hydroxides or alkaline-earth metal hydroxides are preferable. In the present invention, these salts may be first prepared, and the prepared salts may be then added to a composition consisting of other components. Otherwise, caffeoylquinic acids and a salt-forming substance may be added to the aforementioned composition separately, and thereafter, salts may be formed therein.

Natural product extracts containing caffeoylquinic acids, and plant extracts containing caffeoylquinic acids, are preferably extracted from plants containing large quantities of caffeoylquinic acids, such as coffee, cabbage, lettuce, artichoke, tomato, eggplant, potato, carrot, apple, pear, plum, peach, apricot, cherry, sunflower, Jew's marrow, or sweet potato.

Specifically, as a green coffee bean extract, "Flavor Holder" manufactured by T. Hasegawa Co., Ltd. may be used. As an apple extract, "Applephenon" manufactured by the Nikka Whisky Distilling Co., Ltd. may be used. As a sunflower seed extract, "Heliant S-100" manufactured by Dainippon Ink and chemicals, Inc. may be used. The contents of such caffeoylquinic acids in the used plant extract are preferably between 1% and 80% by weight, more preferably between 1% and 50% by weight, and even more preferably between 1% and 40% by weight, in terms of an antihypertensive effect.

Isoflavone extracted from soy beans may preferably be used. As isoflavone that can be easily dissolved in the liquid seasoning, glycosides such as prunetin (5,4'-dihydroxy-7-methoxy body) or irigenin (5,7,3'-trihydroxy-6,4',5'-trimethoxy body) may preferably be used.

The amount of polyphenols mixed into the liquid seasoning of the present invention is preferably between 0.1% and 5% by weight, more preferably between 0.2% and 3% by weight, and even more preferably between 0.5% and 2% by weight, in terms of the antihypertensive effect and flavor. Herein, the amount of polyphenols mixed means the amount of polyphenols added to the liquid seasoning. If the amount of polyphenol is less than 0.1% by weight, a sufficient antihypertensive effect cannot be obtained. In contrast, if the amount of polyphenol is more than 5% by weight, it is not preferable because it results in a strong abnormal taste.

As a peptide having angiotensin converting enzyme inhibitory activity, those derived from food product materials may be used. A peptide derived from milk, a peptide derived from cereal, and a peptide derived from fish, are preferable. Herein, as a peptide derived from cereal, a peptide derived from cereal having a molecular weight between 200 and 4,000, and particularly, a peptide derived from corn having a molecular weight between 200 and 4,000, are preferable. Moreover, a peptide with a molecular weight between 200 and 4,000 obtained by treating a corn protein, soybean protein, wheat protein, or the like with a protease, and a peptide with a molecular weight between 200 and 4,000 obtained by treating a corn protein with an alkaline protease, are preferable (JP-A-7-284369). As a peptide derived from fish, a peptide derived from fish with a molecular weigh between 200 and 10, 000 is preferable. A peptide with a molecular weight between 200 and 10,000,which is obtained by treating fish such as mackerel, oceanic bonito, tuna, or saury with a protease, may be more preferably used. More preferably, a peptide with a molecular weight between 200 and 10,000, which is obtained by treating a bonito protein with a protease, may be used.

The strength of an angiotensin converting enzyme inhibitory activity is indicated by a concentration necessary for inhibiting 50% of the angiotensin converting enzyme activity (IC50). When the IC50 of a peptide having an angiotensin converting enzyme inhibitory activity used in the present invention is approximately between 50 and 1,000 μg/ml, it may be anticipated that the peptide exhibits an antihypertensive effect in a low salt soy sauce system.

Examples of commercially available peptide products that may be used in the present invention include: Peptino (Nihon Shokuhin Kako Co., Ltd.; IC50: 130 μg/ml) which is a peptide derived from corn; Glutamine Peptide GP-1 (Nisshin Pharma; IC50: 508 μg/ml) which is a peptide derived from wheat; Hinute (Fuji Oil Co., Ltd.; IC50: 455 μg/ml) which is a peptide derived from soybeans; and Peptide Straight (Nippon Supplement, Inc.; IC50; 215 μg/ml) which is a peptide derived from oceanic bonito.

The angiotensin converting enzyme inhibitory activity of the above peptide may be measured by ACE Color (Fujirebio Inc.), which is a measurement kit that is easy to handle and has good repeatability using the synthetic substrate p-hydroxybenzoyl-glycyl-L-histidyl-L-leucine. The amount of the above peptide added is preferably between 0.5% and 20% by weight, more preferably between 1% and 10% by weight, and even more preferably between 2% and 5% by weight, based on the total weight of the liquid seasoning, in terms of the antihypertensive effect and flavor.

Examples of a sympathoinhibitory substance used herein include γ-aminobutyric acid, taurine, and salts thereof. As such γ-aminobutyric acid, not only γ-aminobutyric acid extracted from food products, but also a product produced by allowing decarboxylase to act on L-glutamic acid-containing food products, may preferably be used. Fish sauce broth, a pressed liquid thereof, and a fermented product from such fish sauce broth, may preferably be used for the liquid seasoning. Moreover, products obtained from fermented soybeans, rice germ, and rice bran may preferably be used for the liquid seasoning of the present invention because such products do not impair the flavor thereof. Furthermore, undercurrent circumstances, γ-aminobutyric acid with a purity of 100% may also be obtained by extraction and purification from a crude product obtained as a result of fermentation. Such γ-aminobutyric acid with a purity of 100% may preferably be used because it does not impair the flavor. The amount of γ-aminobutyric acid added is preferably between 0.05% and 5% by weight, more preferably between 0.2% and 3% by weight, and even more preferably between 0.5% and 2% by weight, based on the total weight of the liquid seasoning of the present invention, in terms of the antihypertensive effect and flavor.

Taurine extracted from food products (fish and shell fish meat) may preferably be used. The amount of taurine added is preferably between 0.05% and 5% by weight, more preferably between 0.2% and 3% by weight, and even more preferably between 0.5% and 2% by weight, based on the total weight of the liquid seasoning of the present invention, in terms of the antihypertensive effect and flavor.

Moreover, the liquid seasoning of the present invention further contains component (E) one or more selected from among a nucleic acid seasoning, an amino acid seasoning other than component (C), an organic acid salt seasoning, an acidulant, an inorganic acid salt, a sweetener, a protein, a whey mineral, and the like, in terns of a synergistic increase in salty taste, a decrease in bitter taste as well as in salt concentration, and an increase in soy sauce flavor.

Specific examples of such a nucleic acid seasoning include 5'-guanylic acid, inosinic acid, 5'-ribonucleotide, uridylic acid, adenylic acid, sodium, potassium and calcium salts thereof, and yeast extract. The content of such a nucleic acid seasoning is preferably between 0% and 0.2% by weight, more preferably between 0.005% and 0.2% by weight, and even more preferably between 0.01% and 0.1% by weight.

Examples of an amino acid seasoning include amino acids other than acidic amino acids, basic amino acids, and their salts. Specific examples include glycine, alanine, phenylalanine, cystine, threonine, tyrosine, isoleucine, sodium salts thereof, and potassium salts thereof. These substances may be mixed to the liquid seasoning of the present invention, singly or in combination of two or more types. When the content of amino acid mixed is calculated relative to free amino acid, glycine is preferably more than 0.3% by weight, alanine is preferably more than 0. 7% by weight, phenylalanine is preferably more than 0.5% by weight, cystine is preferably more than 0% by weight, threonine is preferably more than 0.3% by weight, tyrosine is preferably more than 0.2% by weight, and isoleucine is preferably more than 0.5% by weight. The upper limit of each of these amino acids is preferably 1.5% or less by weight. Among them, isoleucine is preferable in terms of duration of the salty taste. The content of isoleucine is preferably between 0.5% and 1% by weight.

Examples of an organic acid salt seasoning include sodium salts and potassium salts of organic acids such as lactic acid, succinic acid, malic acid, tartaric acid, or gluconic acid. Among others, disodium succinate and sodium gluconate are particularly preferable. The content of such a substance is preferably between 0% and 0.3% by weight, and more preferably between 0.05% and 0.2% by weight.

Examples of an acidulant include lactic acid, succinic acid, malic acid, citric acid, and tartaric acid. Of these, lactic acid, malic acid, citric acid are preferable, and lactic acid is more preferable. The content of lactic acid is preferably between 0% and 2% by weight, and more preferably between 0.3% and 1% by weight. The content of malic acid and citric acid are preferably between 0% and 0.2% by weight, and more preferably between 0.02% and 0.1% by weight.

Examples of an inorganic acid salt used herein include calcium chloride, magnesium chloride, sodium sulfate, ferrous sulfate, magnesium sulfate, and a potassium alum salt. These substances may be used singly or in combination of two or more types. The content of such an inorganic acid salt in the liquid seasoning of the present invention is preferably between 0.1% and 5% by weight, and more preferably between 0.2% and 2% by weight, based on the total weight, in terms of the improvement of soy sauce flavor such as an increase in the salty taste or a decrease in the abnormal taste or bitter taste.

Examples of a sweetener include fructose, glucose, trehalose, a licorice extract, sugar alcohol (sorbitol, mannitol, maltitol, reduced palatinose, xylitol, etc.), sodium glycyrrhizinate, and a stevia extract. These substances may be used singly or in combination of two or more types. The content of such a stevia extract, licorice extract, or sodium glycyrrhizinate in the liquid seasoning of the present invention is preferably between 0.0001% and 0.1% by weight, and more preferably between 0.0005% and 0.01% by weight, based on the total weight, in terms of the improvement of soy sauce flavor such as an increase in the salty taste or a decrease in the abnormal taste or bitter taste. In the case of other sweeteners, the content thereof in the liquid seasoning of the present invention is preferably between 0.1% and 2% by weight, and more preferably between 0.2% and 1% by weight, based on the total weight, in terms of the improvement of soy sauce flavor such as an increase in the salty taste or a decrease in the abnormal taste or bitter taste.

As a protein, water-soluble proteins such as gelatin are preferably used. Such proteins may be used singly or in combination of two or more types. The content of such a protein in the liquid seasoning of the present invention is preferably between 0.1% and 2% by weight, and more preferably between 0.2% and 1% by weight, based on the total weight, in terms of the improvement of soy sauce flavor such as an increase in the salty taste or a decrease in the abnormal taste or bitter taste.

The content of phytic acid in the liquid seasoning of the present invention is preferably between 0.1% and 2% by weight, and more preferably between 0.2% and 1% by weight, based on the total weight, in terms of the improvement of soy sauce flavor such as an increase in the salty taste or a decrease in the abnormal taste or bitter taste.

The content of whey mineral in the liquid seasoning of the present invention is preferably between 0.1% and 5% by weight, and more preferably between 0.2% and 2% by weight, based on the total weight, in terms of the improvement of soy sauce flavor such as an increase in the salty taste or a decrease in the abnormal taste or bitter taste.

In addition, the pH of the liquid seasoning of the present invention is preferably between pH 3 and 6.5, more preferably between pH 4 and 6, and even more preferably between 4.5 and 5.5, in terms of the prevention of deterioration of the flavor. Moreover, the liquid seasoning of the present invention preferably has specific values such as a chlorine content between 4% and 9% by weight and a solid content between 20% and 45% by weight.

Furthermore, as additives used for increasing the salty taste, ammonium chloride and calcium lactate also have certain effects. However, when the mixed soy sauce is then cooked by heating, the former generates an abnormal taste and the latter causes inconvenience such that the cooked food becomes hardened. Thus, it is not preferable to add these additives to soy sauce having functions as a general-purpose seasoning.

Further, other additives such as ethanol, Japanese sweet rice wine, fermented vinegar, or a sweetener may also be added to the liquid seasoning of the present invention, depending on preferences. Thus, the above liquid seasoning may be processed into various soy sauce processed food products such as seasoning soy sauce or mop sauce.

The liquid seasoning of the present invention exhibits the effect of significantly improving hypertension, when it is continuously ingested. Accordingly, it is possible to describe on a vessel containing the liquid seasoning of the present invention the following messages. "this is suitable for those who are worried about blood pressure," "this is suitable for those who have relatively high blood pressure," "this acts to decrease blood pressure," "this has action to control blood pressure," etc.

EXAMPLES

The present invention will be described more in detail in the following examples. The examples are provided for illustrative purposes only, and are not intended to limit the scope of the invention.

[Preparation of Base Soy Sauce]

A commercially available low salt soy sauce D (nitrogen concentration: 1.5% by weight; sodium concentration: 3.18% by weight (common salt concentration:8.1% by weight); and potassium concentration: 0.38% by weight) was concentrated under a reduced pressure. The concentrated soy sauce was finally adjusted with volatile water and common salts, resulting in a nitrogen concentration of 1.8% by weight, a sodium concentration of 3.34% by weight (a common salt concentration of 8.5% by weight), and a potassium concentration of 0.45% by weight, thereby producing a low salt soy sauce A. In addition, a commercially available low salt soy sauce C (nitrogen concentration: 1.4% by weight; sodium concentration: 3.18% by weight (common salt concentration: 8.1% by weight); and potassium concentration: 0.26% by weight) was concentrated under a reduced pressure. The concentrated soy sauce was finally adjusted with volatile water and common salts, resulting in a nitrogen concentration of 1.85% by weight, a sodium concentration of 3.30% by weight (a common salt concentration of 8.4% by weight), and a potassium concentration of 0.33% by weight, thereby producing a low salt soy sauce B.

(1) Test Examples 1 to 35

The thus produced low salt soy sauces were used as base soy sauces. To each of these base soy sauces, potassium chloride, histidine hydrochloride, sodium aspartate, sodium glutamate, an acidulant, a nucleic acid seasoning, a food material having an antihypertensive effect, and the like, were added.

In addition, as such antihypertensive materials, polyphenol preparation A (which was obtained by extracting from green robusta coffee beans using hot water for 4 hours and treating the obtained extract with an adsorbent (activated carbon or clay) for concentration, followed by spray drying; caffeoylquinic acids; approximately 40%), polyphenol preparation B (which was obtained by subjecting Flavor Holder RC-30 manufactured by T. Hasegawa Co., Ltd. to spray drying; caffeoylquinic acids: approximately 54%), γ-aminobutyric acid, peptide A (Peptide Straight manufactured by Nippon Supplement, Inc.), and peptide B (Peptino manufactured by Nihon Shokuhin Kako Co., Ltd) were added to the base soy sauces, so as to prepare liquid seasonings with compositions shown in Table 1.

(2) Measurement of Sodium Content

The content of sodium was measured using an atomic absorption spectrophotometer (Hitachi Polarization Zeeman Atomic Absorption Spectrophotometer Z-6100). The content of common salt was obtained by converting the obtained value of the sodium content.

(3) Measurement of Potassium Content

The content of potassium was measured in the same manner as that for the aforementioned sodium concentration.

(4) Measurement of Amino Acid Content

The content of amino acid in the total system was measured using an amino acid analyzer (Hitachi L-8800). In the table, the values of the amino acid content in the liquid seasonings other than the food material having an antihypertensive effect (D) are shown.

(5) Measurement of Nitrogen Content

The concentration of nitrogen was measured using a total nitrogen analyzer (Mitsubishi Chemical Corp. TN-05). In the table, the values of nitrogen content in the liquid seasonings other than the food material having an antihypertensive effect (D) are shown.

(6) Sensory Evaluation Procedure

Ten panelists performed sensory evaluation on the obtained low salt soy sauces, in terms of salty taste and bitter taste. Moreover, the soy sauces were also subjected to a comprehensive evaluation, in which the general quality of soy sauce was evaluated. Evaluation standards are shown below. The obtained results are shown in Table 1.

[Evaluation Standards for Salty Taste]
1: The same level as that of low salt soy sauce (corresponding to 9% by weight of common salt)
2: An intermediate level between low salt soy sauce and regular soy sauce (common product) (corresponding to 14% by weight of common salt)
3: Slightly weaker than a regular product (common product)
4: The same level as that of a regular product (common product)
5: Stronger than a regular product (common product) [Evaluation standards for bitter taste]
1: None
2: Very slightly felt
3: Slightly felt
4: Felt
5: Strongly felt

[Evaluation Standards for Abnormal Taste]
1: None
2: Very slightly felt
3: Slightly felt
4: Felt
5: Strongly felt

[Criteria of Judgment in Comprehensive Evaluation]
E: It has a salty taste (4 or more), but does not have a bitter taste and abnormal taste (1 or less)
G: It has a salty taste (4 or more), and has a slight extent of bitter taste and abnormal taste (2 or less)
M: It has a weak salty taste (1 or less) but does not have a bitter taste and abnormal taste (1 or less), or it has rather a weak salty taste (3 or less) and has a slight extent of bitter taste and abnormal taste (3 or less)
P: It has a bitter taste and abnormal taste (3 or more)

TABLE 1

| | | Test examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Raw material (weight %) | Low salt soy sauce A | 93.6 | 93.2 | 92.6 | 93.4 | 92.9 | 93.3 | 92.8 | 88.8 | 88.8 | | | |
| | Low salt soy sauce B | | | | | | | | | | 93.8 | 93.0 | 90.7 |
| | Low salt soy sauce C | | | | | | | | | | | | |
| | Low salt soy sauce D | | | | | | | | | | | | |
| | Potassium chloride | 4 | 4 | 4 | 4 | 4 | 4 | 4 | 4 | 4 | 3 | 3 | 5 |
| | Lactic acid | 0.45 | 0.45 | 0.45 | 0.45 | 0.45 | 0.45 | 0.45 | 0.45 | 0.45 | 0.5 | 0.5 | 0.5 |
| | Citric acid | 0.05 | 0.05 | 0.05 | 0.05 | 0.05 | 0.05 | 0.05 | 0.05 | 0.05 | 0.04 | 0.04 | 0.04 |
| | Malic acid | 0.05 | 0.05 | 0.05 | 0.05 | 0.05 | 0.05 | 0.05 | 0.05 | 0.05 | 0.04 | 0.04 | 0.04 |
| | Disodium succinate | 0.08 | 0.08 | 0.08 | 0.08 | 0.08 | 0.08 | 0.08 | 0.08 | 0.08 | 0.06 | 0.06 | 0.06 |
| | Disodium inosinate | 0.04 | 0.04 | 0.04 | 0.04 | 0.04 | 0.04 | 0.04 | 0.04 | 0.04 | 0.05 | 0.05 | 0.05 |
| | Histidine hydrochloride | | | | | | | | | | | 0.2 | |
| | Sodium aspartate monohydrate | 1 | 1 | 1 | 1 | 1 | 1 | 1 | 1 | 1 | 1.3 | 1.3 | 1.2 |
| | Sodium glutamate monohydrate | 0.5 | 0.5 | 0.5 | 0.5 | 0.5 | 0.5 | 0.5 | 0.5 | 0.5 | 0.6 | 0.6 | 0.6 |
| Antihypertensive material (weight %) | Polyphenol preparation A | 0.25 | 0.63 | 1.25 | | | | | | | 0.63 | 1.25 | |
| | Polyphenol preparation B | | | | 0.46 | 0.92 | | | | | | | 1.85 |
| | γ-aminobutyric acid | | | | | | 0.5 | 1 | | | | | |
| | Peptide A | | | | | | | | 5 | | | | |
| | Peptide B | | | | | | | | | 5 | | | |
| Analytical value (weight %) | Sodium concentration | 3.35 | 3.37 | 3.31 | 3.34 | 3.32 | 3.34 | 3.32 | 3.19 | 3.19 | 3.36 | 3.34 | 3.25 |
| | Common salt concentration | 8.52 | 8.49 | 8.43 | 8.50 | 8.46 | 8.50 | 8.45 | 8.11 | 8.11 | 8.56 | 8.49 | 8.27 |
| | Potassium concentration | 2.52 | 2.52 | 2.52 | 2.52 | 2.52 | 2.52 | 2.52 | 2.50 | 2.50 | 1.88 | 1.88 | 2.92 |
| | Nitrogen concentration | 1.81 | 1.80 | 1.79 | 1.80 | 1.80 | 1.80 | 1.80 | 1.72 | 1.72 | 1.89 | 1.88 | 1.83 |
| | Acidic amino acid | 2.94 | 2.93 | 2.92 | 2.94 | 2.93 | 2.94 | 2.93 | 2.85 | 2.85 | 2.78 | 2.77 | 2.66 |
| | Basic amino acid | 0.94 | 0.93 | 0.93 | 0.93 | 0.93 | 0.93 | 0.93 | 0.89 | 0.89 | 0.94 | 1.10 | 0.91 |
| | Free amino acid | 8.09 | 8.06 | 8.01 | 8.07 | 8.04 | 8.07 | 8.03 | 7.74 | 7.74 | 8.88 | 8.82 | 8.56 |
| | Aspartic acid | 1.44 | 1.44 | 1.44 | 1.44 | 1.44 | 1.44 | 1.44 | 1.41 | 1.41 | 1.12 | 1.12 | 1.04 |
| | Glutamic acid | 1.51 | 1.50 | 1.49 | 1.50 | 1.50 | 1.50 | 1.50 | 1.45 | 1.45 | 1.69 | 1.68 | 1.65 |
| Calculated value | Asp/K | 0.57 | 0.57 | 0.57 | 0.57 | 0.57 | 0.57 | 0.57 | 0.56 | 0.56 | 0.60 | 0.60 | 0.36 |
| | Asp/N | 0.80 | 0.80 | 0.80 | 0.80 | 0.80 | 0.80 | 0.80 | 0.82 | 0.82 | 0.59 | 0.60 | 0.57 |
| Evaluation | Salty taste | 4 | 4 | 4 | 4 | 4 | 4 | 4 | 4 | 4 | 4 | 4 | 4 |
| | Bitter taste | 1 | 1 | 1 | 1 | 1 | 1 | 1 | 2 | 2 | 1 | 1 | 1 |
| | Abnormal taste | 1 | 1 | 1 | 1 | 1 | 1 | 1 | 2 | 2 | 1 | 1 | 1 |
| | Comprehensive evaluation | E | E | E | E | E | E | E | G | G | E | E | E |

TABLE 1-continued

|  |  | Test examples | | | | | | | | | | | |
| --- | --- | --- | --- | --- | --- | --- | --- | --- | --- | --- | --- | --- | --- |
|  |  | 13 | 14 | 15 | 16 | 17 | 18 | 19 | 20 | 21 | 22 | 23 | 24 |
| Raw material (weight %) | Low salt soy sauce A | | | | | | | | | | | | |
|  | Low salt soy sauce B | 93.9 | 91.9 | 94.2 | 94.3 | 92.3 | | | | | | | |
|  | Low salt soy sauce C | | | | | | 100 | | 99.4 | 98.8 | | 99.5 | 95 |
|  | Low salt soy sauce D | | | | | | | 100 | | | 99.5 | | |
|  | Potassium chloride | 3 | 3 | 4 | 4 | 4 | | | | | | | |
|  | Lactic acid | 0.5 | 0.5 | 0.5 | 0.5 | 0.5 | | | | | | | |
|  | Citric acid | 0.04 | 0.04 | 0.05 | 0.05 | 0.05 | | | | | | | |
|  | Malic acid | 0.04 | 0.04 | 0.05 | 0.05 | 0.05 | | | | | | | |
|  | Disodium succinate | 0.06 | 0.06 | 0.06 | 0.06 | 0.06 | | | | | | | |
|  | Disodium inosinate | 0.05 | 0.05 | 0.05 | 0.05 | 0.05 | | | | | | | |
|  | Histidine hydrochloride | | | 0.5 | 0.5 | 0.5 | | | | | | | |
|  | Sodium aspartate monohydrate | 1.3 | 1.3 | | | | | | | | | | |
|  | Sodium glutamate monohydrate | 0.6 | 0.6 | | | | | | | | | | |
| Antihypertensive material (weight %) | Polyphenol preparation A | | | 0.63 | | | | | 0.63 | 1.25 | | | |
|  | Polyphenol preparation B | | | | | | | | | | 0.46 | | |
|  | γ-aminobutyric acid | 0.5 | | | 0.5 | | | | | | | 0.5 | |
|  | Peptide A | | 2.5 | | | 2.5 | | | | | | | 5 |
|  | Peptide B | | | | | | | | | | | | |
| Analytical value (weight %) | Sodium concentration | 3.37 | 3.31 | 3.13 | 3.14 | 3.07 | 3.19 | 3.20 | 3.17 | 3.18 | 3.18 | 3.17 | 3.03 |
|  | Common salt concentration | 8.57 | 8.41 | 7.97 | 7.98 | 7.81 | 8.11 | 8.13 | 8.06 | 8.01 | 8.09 | 8.07 | 7.70 |
|  | Potassium concentration | 1.89 | 1.88 | 2.41 | 2.41 | 2.40 | 0.26 | 0.38 | 0.25 | 0.25 | 0.38 | 0.25 | 0.24 |
|  | Nitrogen concentration | 1.89 | 1.86 | 1.86 | 1.87 | 1.83 | 1.42 | 1.51 | 1.41 | 1.40 | 1.50 | 1.41 | 1.35 |
|  | Acidic amino acid | 2.79 | 2.76 | 1.32 | 1.32 | 1.29 | 1.10 | 1.60 | 1.09 | 1.09 | 1.59 | 1.09 | 1.05 |
|  | Basic amino acid | 0.94 | 0.92 | 1.37 | 1.37 | 1.35 | 0.80 | 0.80 | 0.79 | 0.79 | 0.80 | 0.80 | 0.76 |
|  | Free amino acid | 8.89 | 8.73 | 7.44 | 7.45 | 7.29 | 6.10 | 6.20 | 6.06 | 6.02 | 6.17 | 6.07 | 5.80 |
|  | Aspartic acid | 1.12 | 1.12 | 0.12 | 0.12 | 0.12 | 0.10 | 0.60 | 0.10 | 0.10 | 0.60 | 0.10 | 0.10 |
|  | Glutamic acid | 1.69 | 1.67 | 1.22 | 1.23 | 1.20 | 1.00 | 1.00 | 0.99 | 0.99 | 1.00 | 1.00 | 0.95 |
| Calculated value | Asp/K | 0.59 | 0.60 | 0.05 | 0.05 | 0.05 | 0.39 | 1.57 | 0.39 | 0.39 | 1.57 | 0.39 | 0.39 |
|  | Asp/N | 0.59 | 0.60 | 0.07 | 0.07 | 0.07 | 0.07 | 0.40 | 0.07 | 0.07 | 0.40 | 0.07 | 0.07 |
| Evaluation | Salty taste | 4 | 4 | 4 | 4 | 4 | 1 | 1 | 1 | 1 | 1 | 1 | 1 |
|  | Bitter taste | 1 | 1 | 1 | 1 | 1 | 1 | 1 | 1 | 1 | 1 | 1 | 4 |
|  | Abnormal taste | 1 | 2 | 1 | 1 | 2 | 1 | 1 | 1 | 1 | 1 | 1 | 4 |
|  | Comprehensive evaluation | E | G | E | E | G | M | M | M | M | M | M | P |

|  |  | Test examples | | | | | | | | | | |
| --- | --- | --- | --- | --- | --- | --- | --- | --- | --- | --- | --- | --- |
|  |  | 25 | 26 | 27 | 28 | 29 | 30 | 31 | 32 | 33 | 34 | 35 |
| Raw material (weight %) | Low salt soy sauce A | 93.8 | 92.6 | | 94.8 | | | | | | | |
|  | Low salt soy sauce B | | | 94.4 | | 95.8 | | | | | | |
|  | Low salt soy sauce C | | | | | | 95.4 | 95.1 | | | 98 | |
|  | Low salt soy sauce D | | | | | | | | 96.5 | 90 | | 95 |
|  | Potassium chloride | 4 | 5 | 3 | 4 | 3 | 4 | 4 | 3 | 5 | 2 | 5 |
|  | Lactic acid | 0.45 | 0.45 | 0.5 | 0.45 | 0.5 | | | | | | |
|  | Citric acid | 0.05 | 0.05 | 0.04 | 0.05 | 0.04 | | | | | | |
|  | Malic acid | 0.05 | 0.05 | 0.04 | 0.05 | 0.04 | | | | | | |
|  | Disodium succinate | 0.08 | 0.08 | 0.06 | 0.08 | 0.06 | | | | | | |
|  | Disodium inosinate | 0.04 | 0.04 | 0.05 | 0.04 | 0.05 | | | | | | |
|  | Histidine hydrochloride | | 0.2 | | 0.5 | 0.5 | | | | | | |
|  | Sodium aspartate monohydrate | 1 | 1 | 1.3 | | | | | | | | |
|  | Sodium glutamate monohydrate | 0.5 | 0.5 | 0.6 | | | | | | | | |
| Antihypertensive material (weight %) | Polyphenol preparation A | | | | | | 0.63 | | | | | |
|  | Polyphenol preparation B | | | | | | | 0.92 | | | | |
|  | γ-aminobutyric acid | | | | | | | | 0.5 | | | |
|  | Peptide A | | | | | | | | | 5 | | |
|  | Peptide B | | | | | | | | | | | |
| Analytical value (weight %) | Sodium concentration | 3.36 | 3.32 | 3.39 | 3.20 | 3.19 | 3.04 | 3.03 | 3.09 | 2.88 | 3.12 | 3.03 |
|  | Common salt concentration | 8.54 | 8.44 | 8.62 | 8.13 | 8.11 | 7.73 | 7.71 | 7.85 | 7.32 | 7.95 | 7.72 |
|  | Potassium concentration | 2.52 | 3.04 | 1.89 | 2.53 | 1.89 | 2.34 | 2.34 | 1.94 | 2.97 | 1.30 | 2.98 |
|  | Nitrogen concentration | 1.81 | 1.79 | 1.90 | 1.83 | 1.90 | 1.35 | 1.35 | 1.46 | 1.36 | 1.39 | 1.43 |
|  | Acidic amino acid | 2.94 | 2.92 | 2.79 | 1.80 | 1.34 | 1.05 | 1.05 | 1.54 | 1.44 | 1.08 | 1.52 |
|  | Basic amino acid | 0.94 | 1.10 | 0.94 | 1.38 | 1.39 | 0.76 | 0.76 | 0.77 | 0.72 | 0.78 | 0.76 |
|  | Free amino acid | 8.11 | 8.02 | 8.93 | 7.02 | 7.57 | 5.82 | 5.80 | 5.98 | 5.58 | 5.98 | 5.89 |
|  | Aspartic acid | 1.44 | 1.44 | 1.12 | 0.68 | 0.12 | 0.10 | 0.10 | 0.58 | 0.54 | 0.10 | 0.57 |
|  | Glutamic acid | 1.51 | 1.50 | 1.70 | 1.13 | 1.25 | 0.95 | 0.95 | 0.97 | 0.90 | 0.98 | 0.95 |
| Calculated value | Asp/K | 0.57 | 0.47 | 0.59 | 0.27 | 0.07 | 0.04 | 0.04 | 0.30 | 0.18 | 0.08 | 0.19 |
|  | Asp/N | 0.80 | 0.80 | 0.59 | 0.37 | 0.07 | 0.07 | 0.07 | 0.40 | 0.40 | 0.07 | 0.40 |

TABLE 1-continued

| Evaluation | | | | | | | | | | | | |
|---|---|---|---|---|---|---|---|---|---|---|---|---|
| | Salty taste | 4 | 4 | 4 | 4 | 4 | 3 | 3 | 2 | 3 | 2 | 3 |
| | Bitter taste | 1 | 1 | 1 | 1 | 1 | 2 | 2 | 2 | 3 | 2 | 3 |
| | Abnormal taste | 1 | 1 | 1 | 1 | 1 | 1 | 1 | 1 | 3 | 1 | 1 |
| | Comprehensive evaluation | E | E | E | E | E | M | M | M | P | M | M |

(7) Assay of Antihypertensive Effect

Test 1

(a) Animals to be Used

Male spontaneous hypertensive rats (SHR) with an age of 16 weeks old were fed under conditions consisting of a room temperature of 25±1° C., a humidity of 55±10% RH, and a lighting period of 12 hours (from 7 o'clock in the morning to 7 o'clock in the evening) (in a rat breeding room).

(b) Administration and Dosage

A normal saline solution was administered to a control group. Administration was carried out via an oral administration route. Using a metallic feeding tube, the liquid seasoning was compulsively administered to the rats. The dosage thereof was set at 5 ml/kg.

(c) Assay Procedure

A group consisting of 3 fasting rats (SHR) was used. The systolic blood pressure of the caudal artery thereof was measured, before and 6 hours after the oral administration of the liquid seasoning, using a commercially available noninvasive blood pressure measuring device used for rats (manufactured by Softron).

(d) Statistical Processing

The obtained measurement results were expressed with the mean value of a changed rate and a standard error (SE), and Student's T-test was then carried out.

In Table 1, the antihypertensive effect of each of Test examples 2, 3, 6, 8, 18, 20, 21, 23, 24 and 25, and a normal saline solution, was analyzed. The results are shown in FIG. 1.

Test 2

(a) Animals to be Used

Male spontaneous hypertensive rats (SHR) with an age of 5 weeks old were fed under conditions consisting of a room temperature of 25±1° C., a humidity of 55±10% RH, and a lighting period of 12 hours (from 7 o'clock in the morning to 7 o'clock in the evening) (in a rat breeding room).

(b) Administration and Dosage

Administration was carried out via an oral administration route. Using a metallic feeding tube, the liquid seasoning was compulsively administered to the rats once a day. The dosage thereof was set at 5 ml/kg.

(c) Assay Procedure

A group consisting of 6 SHR rats (with an age of 6 weeks old when the test was initiated) was used. The systolic blood pressure of the caudal artery thereof was measured, once a week, over 6 weeks, using a commercially available noninvasive blood pressure measuring device used for rats (manufactured by Softron).

(d) Statistical Processing

The obtained measurement results were expressed with the mean value of a changed rate and a standard error (SE), and Student's T-test was then carried out.

In Table 1, the antihypertensive effect of each of Test examples 4, 18, and 25 was analyzed. The results are shown in FIG. 2.

Figure 2:
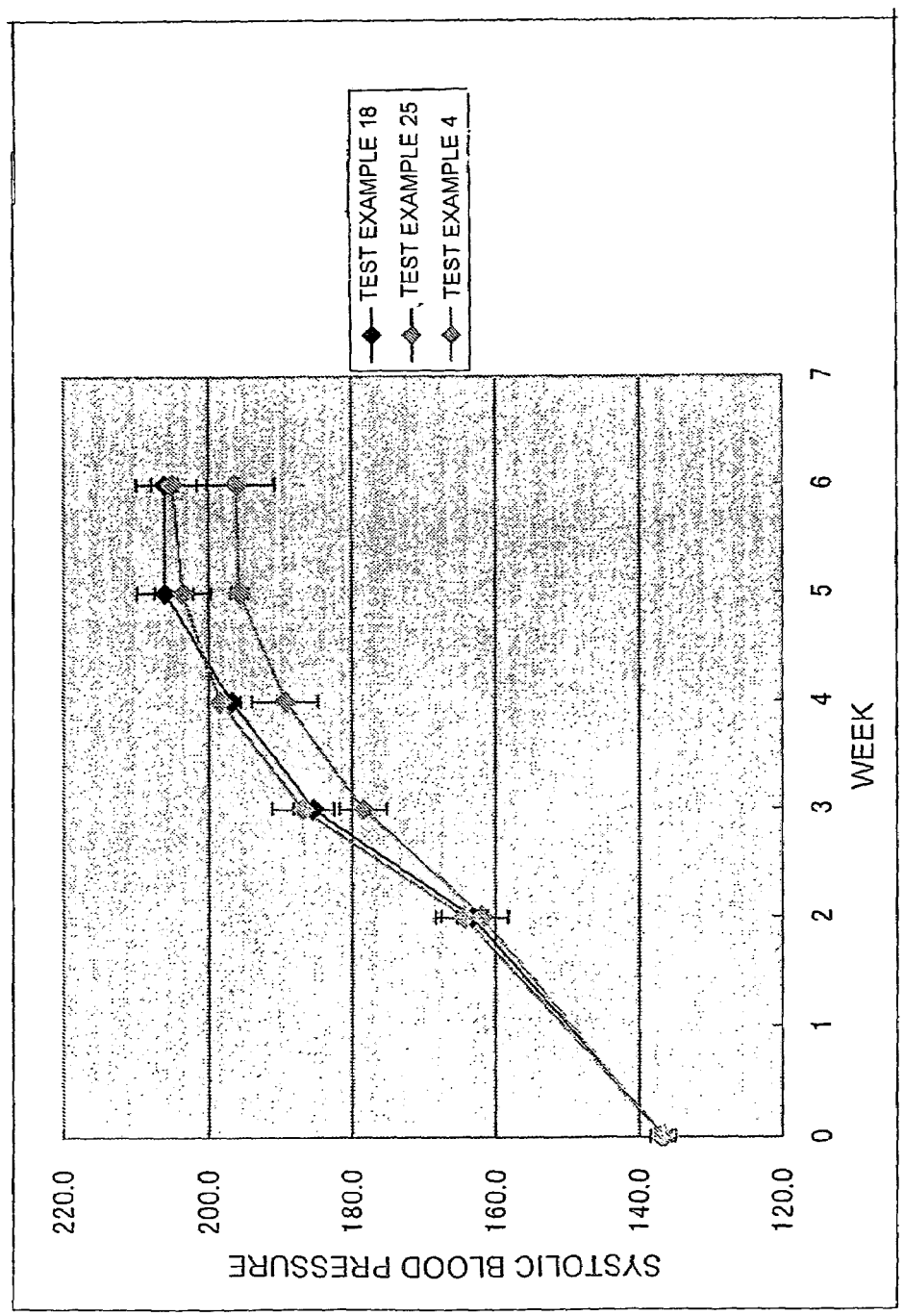
FIG. 2 shows a change in the systolic blood pressure of the rat due to the continuous ingestion of the example liquid seasoning of the present invention.

As is apparent from FIGS. 1 and 2, it was found that the blood pressure is decreased by ingestion of the liquid seasoning of the present invention, and that an increase in the blood pressure was suppressed by continuous ingestion thereof. (In FIGS. 1 and 2, the liquid seasonings of Test examples 18 and 25 contain no food products having an antihypertensive effect.) Moreover, as is clear from Table 1, it was found that even in the case of a liquid seasoning, which has a low common salt concentration and to which a food material having an antihypertensive effect is mixed, the liquid seasoning is able to bring on a sufficient salty taste by adjusting the potassium concentration to the range in the invention of the present application and by using a specific acidic amino acid and specific basic amino acid in combination, and thus that the liquid seasoning reaches a level sufficient for being continuously ingested as soy sauce.

Test 3

(a) Preparation of Soy Sauce

A commercially available low salt soy sauce was concentrated under a reduced pressure. The concentrated soy sauce was finally adjusted with volatile water and common salts, resulting in a nitrogen concentration of 1.8% by weight, a sodium concentration of 3.34% by weight (common salt concentration of 8.5% by weight), and a potassium concentration of 0. 45% by weight, thereby producing low salt soy sauce with a high nitrogen content. Flavor Holder RC-30 manufactured by T. Hasegawa Co., Ltd. was used as a green coffee bean extract (hereinafter referred to as GCE), and it was added to the above produced low salt soy sauce by spray drying, resulting in approximately 54% by weight of chlorogenic acids contained therein. Liquid seasonings shown in Table 2 were prepared, and such liquid seasonings were then subjected to a clinical test using humans.

TABLE 2

| | | Placebo group | Test groups | | |
|---|---|---|---|---|---|
| | | GCE 0 mg | GCE 46 mg | GCE 93 mg | GCE 185 mg |
| Mixing rate (weight %) | High nitrogen low salt soy sauce | 93.84 | 93.38 | 92.91 | 91.99 |
| | Potassium chloride | 4 | 4 | 4 | 4 |
| | Lactic acid | 0.45 | 0.45 | 0.45 | 0.45 |
| | Citric acid | 0.045 | 0.045 | 0.045 | 0.045 |
| | Malic acid | 0.045 | 0.045 | 0.045 | 0.045 |

TABLE 2-continued

|  |  | Placebo group | Test groups | | |
|---|---|---|---|---|---|
|  |  | GCE 0 mg | GCE 46 mg | GCE 93 mg | GCE 185 mg |
|  | Disodium succinate | 0.08 | 0.08 | 0.08 | 0.08 |
|  | Disodium inosinate | 0.04 | 0.04 | 0.04 | 0.04 |
|  | Sodium glutamate | 0.5 | 0.5 | 0.5 | 0.5 |
|  | Sodium aspartate | 1 | 1 | 1 | 1 |
|  | Green coffee bean extract 1) | — | 0.46 | 0.93 | 1.85 |
|  | (Chlorogenic acids) | (0) | (0.25) | (0.50) | (1.00) |
| Analytical value (weight %) | Sodium concentration | 3.35 | 3.34 | 3.32 | 3.29 |
|  | Common salt concentration | 8.54 | 8.50 | 8.46 | 8.38 |
|  | Potassium concentration | 2.52 | 2.52 | 2.52 | 2.52 |
|  | Nitrogen concentration | 1.81 | 1.80 | 1.80 | 1.78 |
|  | Acidic amino acid | 2.94 | 2.94 | 2.93 | 2.91 |
|  | Basic amino acid | 0.94 | 0.93 | 0.93 | 0.92 |
|  | Aspartic acid | 1.44 | 1.44 | 1.44 | 1.43 |
|  | Glutamic acid | 1.51 | 1.50 | 1.50 | 1.49 |
| Calculated value | Asp/K | 0.57 | 0.57 | 0.57 | 0.57 |
|  | Asp/N | 0.80 | 0.80 | 0.80 | 0.80 |
| Nutritional ingredient in 10 g of test meal | Energy (kJ) | 45.6 | 46.9 | 46.5 | 48.1 |
|  | Carbohydrate (g) | 1.1 | 1.14 | 1.15 | 1.23 |
|  | Lipid (g) | 0 | 0 | 0 | 0 |
|  | Protein (g) | 1.01 | 1.02 | 1.02 | 1.03 |
|  | Sodium (g) | 0.35 | 0.35 | 0.35 | 0.35 |
|  | Potassium (g) | 0.25 | 0.25 | 0.25 | 0.25 |
|  | Alcohol (g) | 0.35 | 0.36 | 0.35 | 0.35 |

1) 54% by weight of chlorogenic acids, 12% by weight of caffeine (b) Subjects to be Evaluated Evaluation was carried out on 117 male humans with an age between 30 and 50 years old, who suffered from a mild stage of hypertension (a systolic blood pressure between 140 and 159 mmHg, and a diastolic blood pressure between 90 and 99 mmHg). It is to be noted that smokers with a level of 15 or more cigarettes/day, heavy drinkers who take 30 g or more of alcohol per day, and patients with liver function failure or kidney function failure were excluded from such subjects.

(c) Test Procedures

[Ingestion Procedure and Amount]

10 g of soy sauce and a freeze-dried product (one selected from among seaweed, tofu, and fired bean-curd) were placed in a bowl, and 180 ml of boiled water was then poured therein. The obtained soup was ingested for breakfast. That is, the GCE content in 10 g of soy sauce was adjusted to be 0 mg, 46 mg, 93 mg, or 185 mg, and the thus obtained soups were given to the aforementioned evaluation subjects who were divided into 4 groups (Table 3).

[Assay Procedure]

Figure 3:
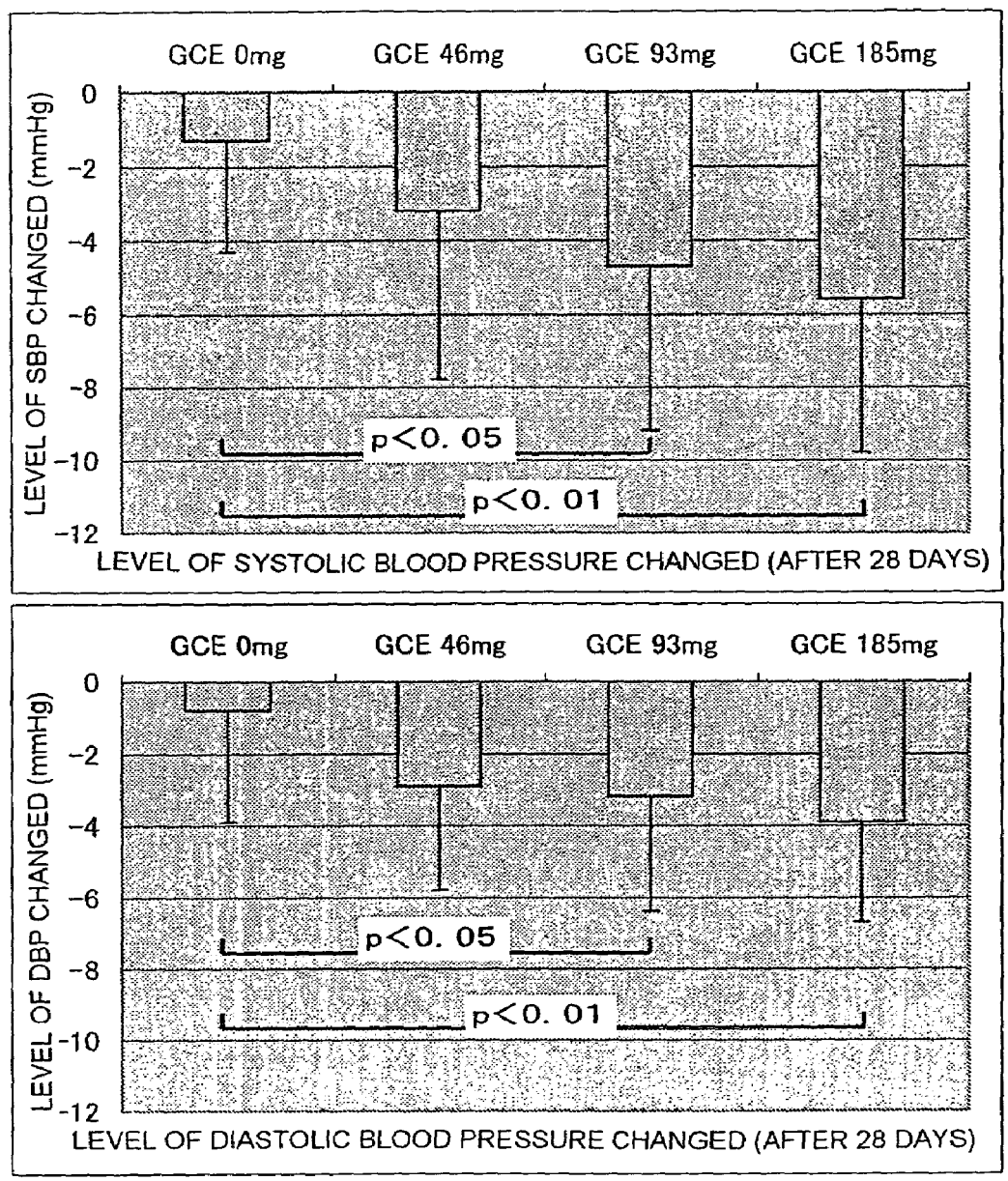
FIG. 3 shows the systolic blood pressure and diastolic blood pressure of a human, which were measured 28 days after the continuous ingestion of the example liquid seasoning of the present invention.

After the subjects had taken a rest for 10 minutes while sitting on a chair, the blood pressure of the right arm was measured three times with an automatic sphygmomanometer. A comparison was made between the systolic blood pressure (SBP) and the diastolic blood pressure (DBP). The median of each value was adopted as a measurement value (FIG. 3).

[Statistical Processing]

The obtained data were subjected to a multiple comparison test, using statistical analysis software, StatView program (version 5.0; SAS Institute Inc., Cary N.C.).

TABLE 3

|  |  | Placebo group | Test groups | | |
|---|---|---|---|---|---|
|  |  | GCE 0 mg | GCE 46 mg | GCE 93 mg | GCE 185 mg |
|  | Number of subjects | 29 | 29 | 28 | 31 |
|  | Age | 43.1 ± 9.1 | 42.9 ± 8.2 | 43.3 ± 8.3 | 43.4 ± 8.4 |
| Initiation of test | Body weight (kg) | 69.9 ± 10.7 | 73.9 ± 13.6 | 70.3 ± 8.1 | 73.6 ± 13.2 |
|  | BMI (kg/m$^2$) | 24.0 ± 3.1 | 25.2 ± 4.0 | 24.4 ± 2.6 | 25.1 ± 3.6 |
|  | SBP (mmHg) | 145.4 ± 5.5 | 145.9 ± 5.1 | 145.7 ± 5.0 | 146.0 ± 5.3 |
|  | DBP (mmHg) | 91.7 ± 2.5 | 92.1 ± 2.7 | 92.5 ± 2.7 | 92.5 ± 2.9 |
|  | Pulse (beats/min.) | 76.3 ± 8.9 | 79.6 ± 7.1 | 75.8 ± 7.7 | 79.5 ± 6.2 |
| Completion of test (28 days later) | Body weight (kg) | 69.7 ± 10.5 | 73.8 ± 13.4 | 70.2 ± 7.9 | 73.6 ± 13.1 |
|  | BMI (kg/m$^2$) | 23.9 ± 3.1 | 25.1 ± 4.0 | 24.4 ± 2.6 | 25.1 ± 3.6 |
|  | Level of SBP changed (mmHg) | −1.3 ± 3.0 | −3.2 ± 4.6 | −4.7 ± 4.5 | −5.6 ± 4.2 |
|  | Level of DBP changed (mmHg) | −0.8 ± 3.1 | −2.9 ± 2.9 | −3.2 ± 3.2 | −3.9 ± 2.8 |
|  | Pulse (beats/min.) | 75.8 ± 1.3 | 76.7 ± 1.1 | 77.1 ± 1.4 | 75.9 ± 1.2 |

Each value is expressed by mean ± SD (d) Analysis of the Results

As shown in Table 3, when the test was initiated, no significant differences were found among the 4 groups (placebo group, GCE 0 mg; test group, GCE 46 mg; test group, GCE 93 mg; and test group, GCE 185 mg), in terms of blood pressure, pulse, age, body weight, BMI, or the like.

As shown in FIG. 3, the levels of SBP changed 28 days after ingestion of the test meal were −1.3±3.0, −3.2±4.6, −4.7±4.5, and −5.6±4.2, in the placebo group (GCE 0 mg), the test group (GCE 46 mg), the test group (GCE 93 mg), and the test group (GCE 185 mg), respectively. Thus, a decrease in the blood pressure was confirmed in all of the 4 groups. It was also confirmed that the test group (GCE 93 mg) and the test group (GCE 185 mg) had significant differences with the placebo group (GCE 0 mg).

Moreover, the levels of DBP changed 28 days after ingestion of the test meal were −0.8±3.1, −2.9±2.9, −3.2±3.2, and −3.9±2.8, in the placebo group (GCE 0 mg), the test group (GCE 46 mg), the test group (GCE 93 mg), and the test group (GCE 185 mg), respectively. Thus, a decrease in the blood pressure was confirmed in all of the 4 groups. Furthermore, it was also confirmed that the test group (GCE 93 mg) and the test group (GCE 185 mg) had significant differences with the placebo group (GCE 0 mg).

From the above results, it was found that the liquid seasoning of the present invention has an antihypertensive effect. From the results of the statistical analysis, it was confirmed that when soy sauce containing 93 mg or more of GCE (50 mg of chlorogenic acids) is ingested at an amount of 10 g/day for approximately 1 month, it exhibits an antihypertensive effect much greater than that of the placebo group.

What is claimed is:

1. A liquid seasoning comprising the following components (A) to (D):
   (A) sodium, the sodium being present in an amount of 3.55% by weight or less based on a total weight of the liquid seasoning;
   (B) potassium in an amount of from 0.5% to 4.2% by weight based on the total weight of the liquid seasoning;
   (C) (i) from 1% to 3% by weight of aspartic acid and (ii) from 1.3% to 2% by weight of glutamic acid, each based on the total weight of the liquid seasoning; and
   (D) from 0.05% to 10% by weight of a peptide having an angiotensin conversion inhibitory activity
   selected from the group consisting of a milk peptide, a peptide derived from cereal, and a peptide derived from fish,
      wherein said peptide derived from cereal has a molecular weight between 200 Da and 4,000 Da and is obtained by treating a corn protein, soybean protein, or wheat protein with a protease, and
      wherein said peptide derived from fish has a molecular weight between 200 Da and 10,000 Da and is obtained by treating mackerel, oceanic bonito, tuna, or saury with a protease; and
   wherein a weight ratio of the aspartic acid to potassium in the liquid seasoning is 0.25 or greater.

2. The liquid seasoning according to claim 1, wherein: component (C) is present in an amount of from greater than 2% to 5% by weight based on the total weight of the liquid seasoning.

3. The liquid seasoning according to claim 1, further comprising a component (E):
   (E) at least one member selected from the group consisting of nucleic acid seasonings, amino acid seasonings other than component (C), organic acid salt seasonings, acidulants, inorganic acid salts, sweeteners, proteins, and whey minerals.

4. The liquid seasoning according to claim 1, wherein the liquid seasoning is a low salt soy sauce.

5. The liquid seasoning according to claim 1, wherein the liquid seasoning further comprises γ-aminobutyric acid or a salt of γ-aminobutyric acid.

6. The liquid seasoning according to claim 1, wherein the liquid seasoning further comprises taurine or a salt of taurine.

7. The liquid seasoning according to claim 1, wherein the liquid seasoning further comprises at least one polyphenol selected from the group consisting of a flavonoid, a tannin, and a phenolic acid.

8. The liquid seasoning according to claim 1, wherein the liquid seasoning further comprises at least one polyphenol selected from the group consisting of caffeoylquinic acids, feruloylquinic acid, flavonols, flavanols, flavanones, flavones, isoflavones, and anthocyanidins.

9. The liquid seasoning according to claim 1, wherein the liquid seasoning further comprises at least one polyphenol at least one polyphenol selected from the group consisting of catechin, epicatechin, gallocatechin, epigallocatechin, rutin, quercitrin, isoquercitrin, quercetin, myricitrin, myricetin, daizein, daizin, glycitein, glycitin, genistein, genistin, myricitrin, hesperidin, methyihesperidin, neohesperidin, hesperetin, naringin, naringenin, prunin, astragalin, kaempferol, apiin, apigenin, deiphinidin, deiphin, nasunin, peonidin, peonin, petunin, peonidin, malvidin, malvin, enin, cyanidin, leucocyanidin, cyanin, chrysanthemin, keracyanin, idein, mecocyanin, pelargonidin, and callistephin; or a acetylated product, a malonylated product, a methylated product, or a sugar-binding product thereof.

10. The liquid seasoning according to claim 1, wherein the liquid seasoning further comprises at least one caffeoylquinic acid selected from the group consisting of 3-caffeoylquinic acid, 4-caffeoylquinic acid, 5-caffeoylquinic acid (chlorogenic acid), 3,4-dicaffeoylquinic acid, 3,5-dicaffeoylquinic acid, 4,5-dicaffeoylquinic acid, 3-feruloylquinic acid, 4-feruloylquinic acid, 5-feruloylquinic acid, and 3-feruloyl-4-caffeoylquinic acid; or a salt thereof.

11. The liquid seasoning according to claim 1, wherein the peptide having an angiotensin conversion inhibitory activity is a milk peptide.

12. The liquid seasoning according to claim 1, wherein the peptide having an angiotensin conversion inhibitory activity is a peptide derived from cereal.

13. The liquid seasoning according to claim 1, wherein the peptide having an angiotensin conversion inhibitory activity is a peptide derived from fish.

14. A liquid seasoning comprising the following components (A) to (D):
   (A) sodium, the sodium being present in an amount of 3.55% by weight or less based on a total weight of the liquid seasoning;
   (B) potassium in an amount of from 0.5% to 4.2% by weight based on the total weight of the liquid seasoning;
   (C) (i) from 1% to 3% by weight of aspartic acid, (ii) from 1% to 2% by weight of glutamic acid, and (iii) from 0.2 to 1% by weight of histidine, each based on the total weight of the liquid seasoning; and
   (D) from 0.0 5% to 10% by weight of a peptide having an angiotensin conversion inhibitory activity selected from the group consisting of a milk peptide, a peptide derived from cereal, and a peptide derived from fish,
      wherein said peptide derived from cereal has a molecular weight between 200 Da and 4,000 Da and is obtained by treating a corn protein, soybean protein, or wheat protein with a protease, and wherein said peptide derived from fish has a molecular weight between 200 Da and 10,000 Da and is obtained by treating mackerel, oceanic bonito, tuna, or saury with a protease; and wherein a weight ratio of the aspartic acid to potassium in the liquid seasoning is 0.25 or greater.

15. The liquid seasoning according to claim 14, wherein:
component (C) is present in an amount of from greater than 2% to 5% by weight based on the total weight of the liquid seasoning.

16. The liquid seasoning according to claim 14, further comprising a component (E):
(E) at least one member selected from the group consisting of nucleic acid seasonings, amino acid seasonings other than component (C), organic acid salt seasonings, acidulants, inorganic acid salts, sweeteners, proteins, and whey minerals.

17. The liquid seasoning according to claim 14, wherein the liquid seasoning is a low salt soy sauce.

18. The liquid seasoning according to claim 14, wherein the liquid seasoning further comprises γ-aminobutyric acid or a salt of γ-aminobutyric acid.

19. The liquid seasoning according to claim 14, wherein the liquid seasoning further comprises taurine or a salt of taurine.

20. The liquid seasoning according to claim 14, wherein the liquid seasoning further comprises at least one polyphenol selected from the group consisting of a flavonoid, a tannin, and a phenolic acid.

21. The liquid seasoning according to claim 14, wherein the liquid seasoning further comprises at least one polyphenol selected from the group consisting of caffeoylquinic acids, feruloylquinic acid, flavonols, flavanols, flavanones, flavones, isoflavones, and anthocyanidins.

22. The liquid seasoning according to claim 14, wherein the liquid seasoning further comprises at least one polyphenol at least one polyphenol selected from the group consisting of catechin, epicatechin, gallocatechin, epigallocatechin, rutin, quercitrin, isoquercitrin, quercetin, myricitrin, myricetin, daizein, daizin, glycitein, glycitin, genistein, genistin, myricitrin, hesperidin, methylhesperidin, neohesperidin, hesperetin, naringin, naringenin, prunin, astragalin, kaempferol, apiin, apigenin, delphinidin, delphin, nasunin, peonidin, peonin, petunin, peonidin, malvidin, malvin, enin, cyanidin, leucocyanidin, cyanin, chrysanthemin, keracyanin, idein, mecocyanin, pelargonidin, and callistephin; or a acetylated product, a malonylated product, a methylated product, or a sugar-binding product thereof.

23. The liquid seasoning according to claim 14, wherein the liquid seasoning further comprises at least one caffeoylquinic acid selected from the group consisting of 3-caffeoylquinic acid, 4-caffeoylquinic acid, 5-caffeoylquinic acid (chlorogenic acid), 3,4-dicaffeoylquinic acid, 3,5-dicaffeoylquinic acid, 4,5-dicaffeoylquinic acid, 3-feruloylquinic acid, 4-feruloylquinic acid, 5-feruloylquinic acid, and 3-feruloyl-4-caffeoylquinic acid; or a salt thereof.

24. The liquid seasoning according to claim 14, wherein the peptide having an angiotensin conversion inhibitory activity is a milk peptide.

25. The liquid seasoning according to claim 14, wherein the peptide having an angiotensin conversion inhibitory activity is a peptide derived from cereal.

26. The liquid seasoning according to claim 14, wherein the peptide having an angiotensin conversion inhibitory activity is a peptide derived from fish.

* * * * *